(12) United States Patent
Shirota et al.

(10) Patent No.: US 9,655,582 B2
(45) Date of Patent: May 23, 2017

(54) RADIOGRAPHIC APPARATUS

(71) Applicant: SHIMADZU CORPORATION, Kyoto-shi Kyoto (JP)

(72) Inventors: Ken Shirota, Kyoto (JP); Toshiaki Nakamura, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 162 days.

(21) Appl. No.: 14/798,991

(22) Filed: Jul. 14, 2015

(65) Prior Publication Data

US 2017/0014092 A1    Jan. 19, 2017

(51) Int. Cl.
*H05G 1/10* (2006.01)
*A61B 6/00* (2006.01)
*A61B 6/10* (2006.01)

(52) U.S. Cl.
CPC ............... *A61B 6/54* (2013.01); *A61B 6/105* (2013.01); *A61B 6/4405* (2013.01)

(58) Field of Classification Search
CPC ... H05G 1/10; H05G 1/54; A61B 6/00; A61B 6/10; A61B 6/54; A61B 6/105; A61B 6/4405; A61B 6/4482

USPC .......................... 378/101, 102, 103, 114, 198
See application file for complete search history.

(56) References Cited

U.S. PATENT DOCUMENTS

2014/0016747 A1*  1/2014  Watanabe ................ A61B 6/56
378/62

FOREIGN PATENT DOCUMENTS

| JP | 2002-336227 | 11/2002 |
|----|-------------|---------|
| JP | 2010-273827 | 12/2010 |
| JP | 2011-131089 | 7/2011  |

* cited by examiner

*Primary Examiner* — Jurie Yun
(74) *Attorney, Agent, or Firm* — Andrew F. Young, Esq.; Lackenbach Siegel, LLP

(57) ABSTRACT

A mobile X-ray radiographic device has an extended operable time by employing a regenerative energy system and assembly. A regenerative brake circuit acts to provide a braking force for a rear wheel set during a circumstance and an adaptive use wherein a driving force is cut off to the rear wheels, and a second battery system charges with the generated electric power for adaptive use. The regenerative brake circuit further acts to provide the braking force for a rotary anode under the circumstance in which the driving force is cut off to the rotary anode and also the second battery charges with the generated electric power.

13 Claims, 3 Drawing Sheets

RADIOGRAPHIC APPARATUS

CROSS REFERENCE TO RELATED APPLICATIONS

This application relates to JP Ser. No. 2013-000946 filed Jan. 8, 2013, the entire contents of which are incorporated herein fully by reference.

FIGURE SELECTED FOR PUBLICATION

FIG. 1

BACKGROUND OF THE INVENTION

Field of the Invention

The present invention relates to a mobile X-ray radiographic device for conducting radiographic imagery while being mobile from a patient room to another patient room in a hospital.

Description of the Related Art

Such mobile X-ray radiographic devices comprises an arm having an X-ray tube on the tip thereof, which is operative in elevating relative to a supporting pole installed on a wheel platform and is movable between patient rooms by an electric driving motor installed on the wheel platform, which is operative to rotate the wheels. A battery installed inside the wheel platform is operative as the electric power supply for the driving motor. Further, the battery is also operative as the electric power supply to provide high voltage for the X-ray tube. Accordingly, the operation time of the X-ray radiographic device depends on the capacity of the battery.

The visiting X-ray radiographic device having a plurality of the rechargeable batteries is disclosed in Patent Document 1, noted below and incorporated herein fully by reference. A portable X-ray device having a lead battery to provide high voltage for the X-ray tube, a lithium battery to recharge the lead battery and so on is disclosed in Patent Document 2, noted below and incorporated herein fully by reference. A visiting X-ray radiographic device having a battery as an electric power supply exclusively for releasing the emergency braking, in addition to the main battery, is disclosed in Patent Document 3, noted below and incorporated herein fully by reference.

PRIOR ART DOCUMENTS

Patent Document

Patent Document 1: JP Patent Published 2002-336227
Patent Document 2: JP Patent Published 2010-273827
Patent Document 3: JP Patent Published 2011-131089

ASPECTS AND SUMMARY OF THE INVENTION

Problems to be Solved by the Invention

Unfortunately, according to Patent Document 1 through Patent Document 3, if the plural batteries having the same functions or different functions are provided, the operable time of the X-ray radiographic device can be longer in accordance with the total capacity of the X-ray radiographic device batteries but the operable time is nonetheless limited depending on the total capacity of batteries.

The present invention is provided to solve the above problem and the purpose thereof is to provide an X-ray radiographic device, wherein the operable time of the device thereof can be longer and extended by employing a regenerative energy system.

Means for Solving the Problem

The proposed invention is characterized in that a visiting X-ray radiographic device includes; a wheel platform, an X-ray tube that installed as operative in elevating relative to the supporting pole installed on the wheel platform, and a driving motor installed on the wheel platform for revolution drive of wheels, and further comprises; the first battery connected to the X-ray tube, which provides necessary electric power to generate X-ray from the X-ray tube within a short period of time for the X-ray tube, a second battery connected to the driving motor, which is less deteriorative than the first battery despite repeating charge and discharge, a regenerative brake circuit connected to the driving motor, and a charge circuit to charge the second battery by utilizing the electric power obtained from the regenerative brake circuit.

According to the proposed invention a conversion circuit is operative to charge relative between a first battery and a second battery by converting each battery output between the first battery and the second battery as noted herein.

According to the proposed invention a first battery is a lead battery.

According to the proposed invention a second battery is a lithium battery.

Effects of the Invention

According to the proposed invention the operation time of the device can be longer by charging the second battery that is less deteriorative despite repeating charge and discharge by applying the regenerative energy relative to the driving motor.

According to the invention of Claim 3, even if either capacity of the first battery or the second battery becomes zero, a part of functions can be complementary and continuously operative by utilizing the other battery.

DETAILED DESCRIPTION OF THE PREFERRED EMBODIMENTS

Figure 1:
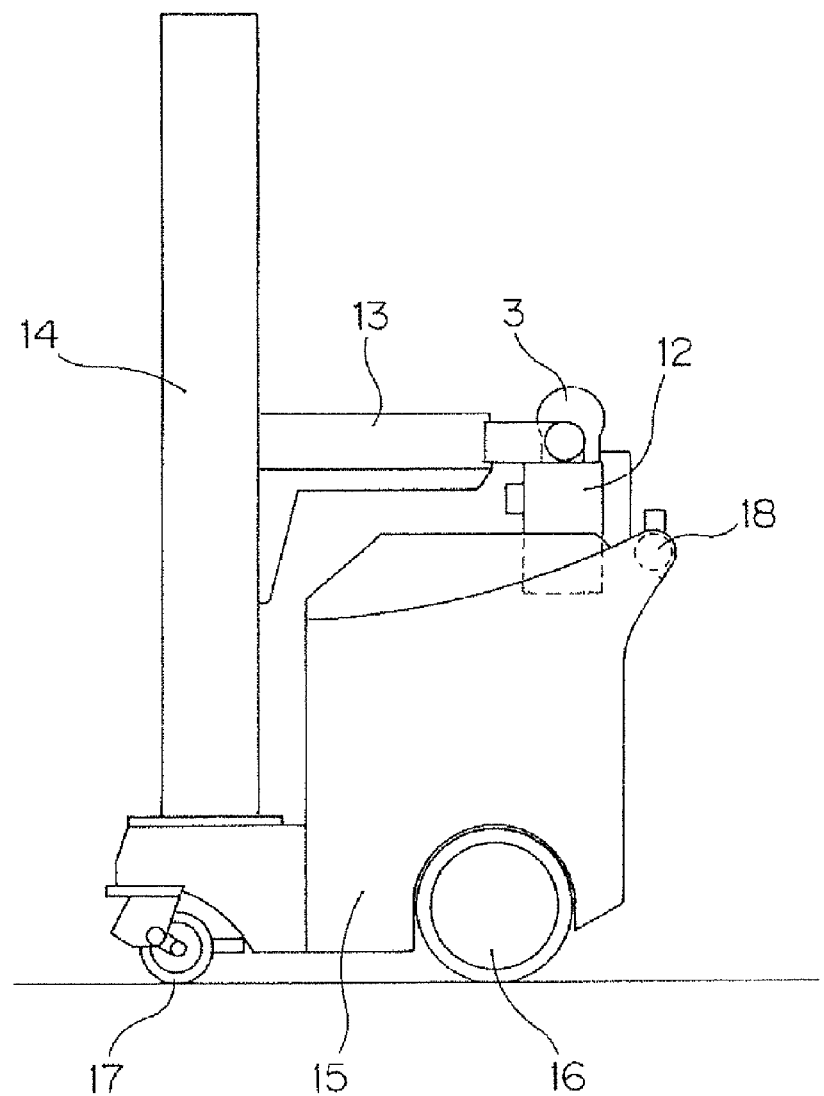
FIG. 1 is a schematic side view of an X-ray radiographic device of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Embodiments

Embodiments of the present invention are now illustrated referring to figures. FIG. 1 is a schematic side view of an X-ray radiographic device of the present invention.

The X-ray radiographic device of the present invention includes a supporting pole 14 installed on the wheel platform 15, an arm 13 installed as operative in elevating relative to the supporting pole 14, an X-ray tube installed at the tip of the arm 13, and a collimator installed below the X-ray tube 3. The X-ray radiographic device constitutes the system, wherein an X-ray shooting is conducted by setting a subject target (not shown but understood by one of skill in the art) between an X-ray detector such as a flat panel detector (also not show but to be understood), and a cassette storing the X-ray film and the X-ray tube in the patient room.

Further, the X-ray radiographic device of the present invention provides a pair of front wheels 17 to change the moving direction and a pair of rear wheels 16 for driving. Further, the X-ray radiographic device of the present invention includes an operation handle 18 operative to handle the direction of travel of the wheel platform 15.

Figure 2:
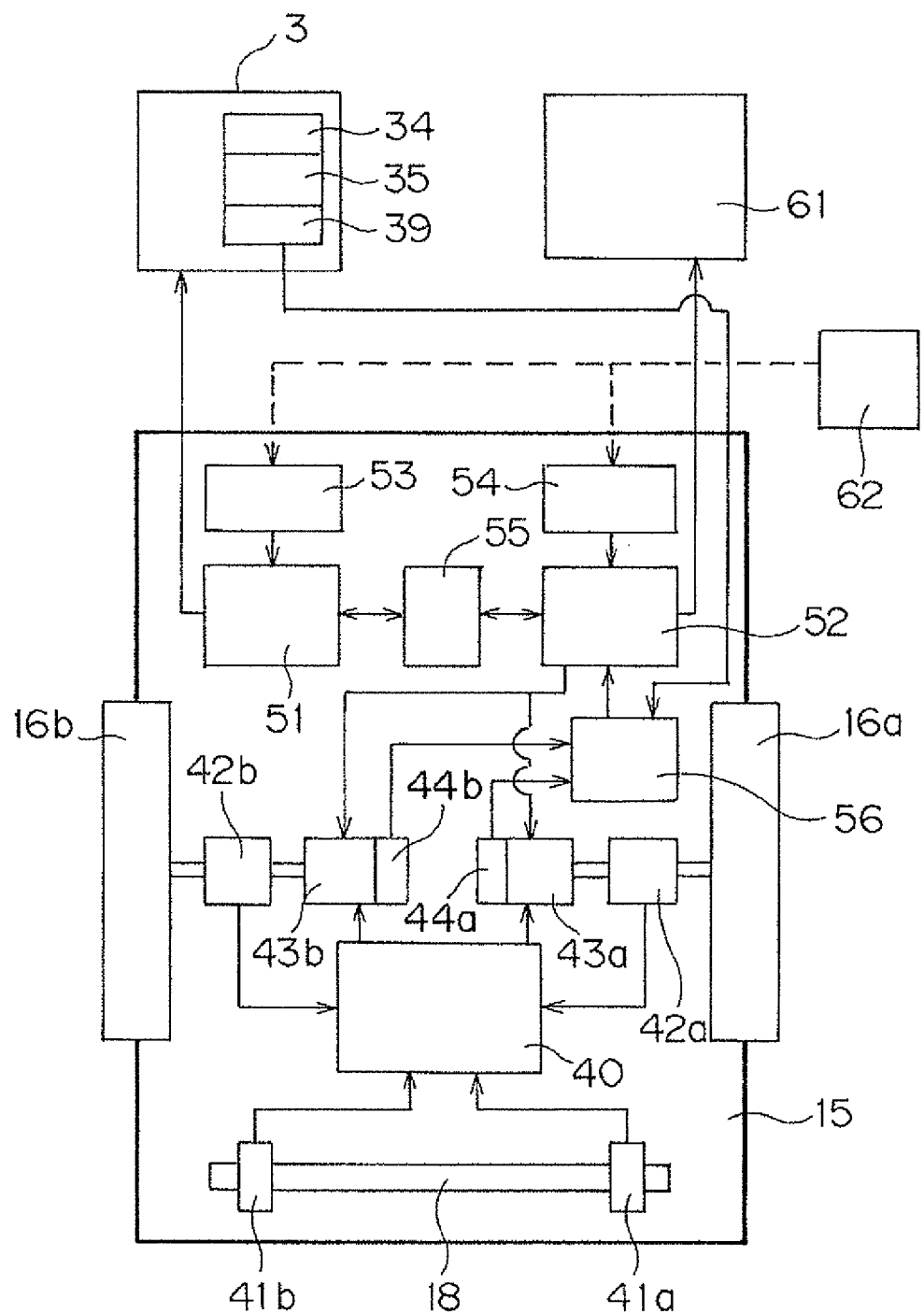
FIG. 2 is a block diagram illustrating the control system of the X-ray radiographic device of the present invention.

FIG. 2 is a block diagram illustrating the control system of the X-ray radiographic device of the present invention.

The X-ray radiographic device of the present invention includes a control module 40 to control the entire device inside the wheel platform 15. The X-ray radiographic device of the present invention includes the first battery 51 and the second battery 52 inside the wheel platform 15.

The first battery 51 can be connected to the commercial power supply 62 through the charge circuit 53 and the second battery 52 can be connected to the commercial power supply 62 through the charge circuit 54. The first battery 51 and the second battery 52 can be operatively charged by the commercial power supply 62 by connecting the power cord inside the wheel platform 15 to the external electric outlet of the commercial power supply 62. The conversion circuit 55 is installed between the first battery 51 and the second battery 52 and operative to be chargeable each other between the first battery 51 and the second battery 52 by converting each other's output between the first battery 51 and the second battery 52. It will be understood that the above components are in an operatively connective condition for such charging and charge transfer.

Here, the first battery 51 is employed mainly to supply the electric power for the X-ray tube 3. As the first battery 51, the battery that can supply a large current needed to generate X-ray from the X-ray tube 3 in a short period of time, e.g., within approximately 1 second, for the X-ray tube is employed. A lead battery as the first battery 51 is employed to achieve such purpose.

On the other hand, the second battery 52 is employed to supply electric power for the driving motor 43a, 43b and the console module 61, as later set forth, for which that electric power is not supplied by the first battery 51. Here, the display module to display the image detected by the X-ray detector is installed to the console module 61. The second battery 52 as a structure charges by utilizing the regenerative energy due to actions of the regenerative brake circuit 39, 44a, 44b and the charge circuit 56, as later set forth. For such purpose, the lithium battery that is less deteriorative than the first battery 51 despite repeating charge and discharge is employed as the second battery 52.

The right side rear wheel 16a of a pair of wheels 16 to drive the wheel platform 15 is connected to the driving motor 43a through the encoder 42a. Similarly, the left rear wheel 16b is connected to the driving motor 43b through the encoder 42b. The encoder 42a, 42b and the driving motor 43a, 43b are connected to the control module 40 and the control module 40 transmits the revolving control signal for the driving motor 43a, 43b based on the revolving speed of the rear wheels 16a, 16b, detected by the encoder 43a, 43b.

Further, a pair of sensors 41a, 41b to detect the operation force given to the operation handle 18 is installed near right end and left end of the operation handle 18 as described above. The sensors 41a, 41b has the structure in which a lever is installed between the pressure sensors installed respectively in an anteroposterior direction and detects forward or backward operation force given by the operator to near the right end or the left end of the handle 18.

The control module 40 controls revolving of a pair of rear wheels 16a, 16b based on the signal of the sensors 41a, 41b. Specifically, when the sensor 41a near the right end of the operation handle 18 detects the operation force forward, the control module 40 sends the signal to the driving motor 43a to revolve the rear wheel 16a for normal revolving and when the sensor 41a near the right end of the operation handle 18 detects the operation force backward, the control module 40 sends the signal to the driving motor 43a to revolve the rear wheel 16a for reverse revolving. Similarly, when the sensor 41b near the left end of the operation handle 18 detects the operation force forward, the control module 40 sends the signal to the driving motor 43b to revolve the rear wheel 16b for revolving and when the sensor 41b near the left end of the operation handle 18 detects the operation force backward, the control module 40 sends the signal to the driving motor 43b to revolve the rear wheel 16a for reverse revolving. And the signal from the control module 40 is the signal as the revolving speed of each driving motor 43a, 43b is proportional to the severity of the operation force to the operation handle 18. Accordingly, the X-ray radiographic device moves in the operational direction in accordance with the operation force given by the operator (understood to be a person directing the device but not shown) to the operation handle 18.

The regenerative brake circuit 44a is connected to the driving motor 43a and the regenerative brake circuit 44b is connected to the driving motor 43b. The regenerative brake circuit 44a, 44b generates electric power with the action of the regenerative brake under the circumstance on which the rear wheel 16a, 16b is revolving without the driving force provided by the driving motor 43a, 43b. When the electric supply for the driving motor 43a, 43b is cut off while the wheel platform is moving due to the revolving of the rear wheel 16a, 16b, the braking force is given to revolving of the rear wheel 16a, 16b by the regenerative brake circuit 44a, 44b and the regeneration brake circuit 44a, 44b acts to generate electric power along with the braking. And the second battery charges with the generated electric power through the charge circuit 56. Further, as described above, the charge circuit 56 is also connected to the regenerative brake circuit 39 relative to the X-ray tube 3.

Figure 3:
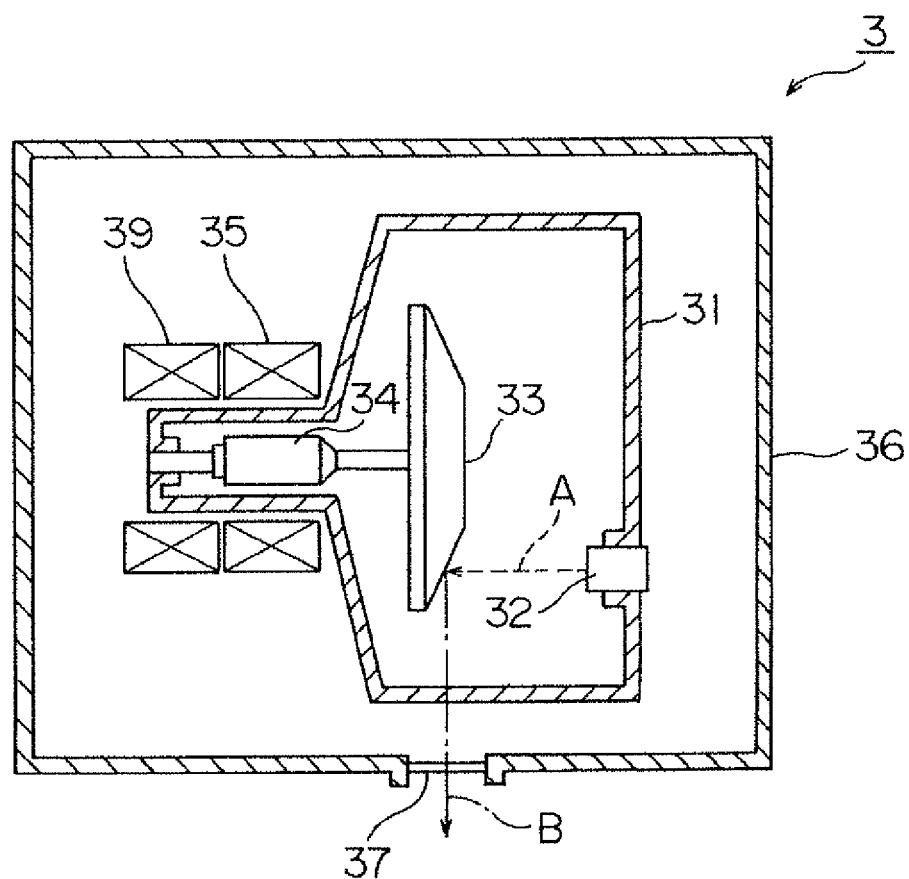
FIG. 3 is a schematic view of the X-ray tube 3.

FIG. 3 is a schematic view of the X-ray tube 3.

The x-ray tube 3 has a radiation window 37 and includes a casing 36 lined inside with lead to block X-ray. The vacuum glass bulb 31 is installed inside the casing 36. The cathode 32 having a pair of filaments, not shown in FIG., to generates a thermion A and a rotary anode (target) 33 to generate X-ray B by receiving the thermion A emitted from the cathode 32 are installed inside the glass bulb 31. The rotary anode 33 is connected to the motor rotor 34. The motor rotor 34 will be rotated in the high speed by the motor stator 35 installed outside the glass bulb 31. With regard to the X-ray tube 3, X-ray B generated from the rotary anode 33 is irradiated through the radiation window 37.

The regenerative brake circuit 39 as described above is connected to the anode motor consisting of the motor rotor 34 and the motor stator 35. The regenerative brake circuit 39 generates electric power with the action of the regenerative brake under the circumstance on which the rotary anode 33 is rotating without the driving force from the anode motor 33 consisting of the motor rotor 34 and the motor stator 3. When the electric power supply for the anode motor is cut off while the rotary anode 33 is rotating, the braking force is given to the rotation of the rotary anode 33 by the regenerative brake circuit 39 and the regenerative brake circuit 39 acts to generate electric power along with the braking. And the second battery 52 charges with the generated electric power through the charge circuit 56.

According to the X-ray radiographic device having the above structure, the regenerative brake circuit 44a, 44b acts to provide the braking force for the rear wheel 16a, 16b under the circumstance on which the driving force is cut off to the rear wheel 16a, 16b and also the second battery 52 charges with the generated electric power thereby. The regenerative brake circuit 39 acts to provide the braking force for the rotary anode 33 under the circumstance on which the driving force is cut off to the rotary anode 33, and also the second battery 52 charges with the generated electric power thereby. Accordingly, charging the second battery 52 providing the electric power for the driving motor 43a, 43b and the console 61 can be conducted while the X-ray radiographic device is being in use. Accordingly, the operable time of the X-ray radiographic device can be extended. Further, the deterioration can be suppressed as minimum despite repeating charge and discharge because the lithium battery is applied as the second battery 52.

Accordingly, the first battery 51 can be exclusively employed to provide electric power for the X-ray tube 3 so that the more X-ray radiographies can be conducted.

Further, since the conversion circuit 55 is installed between the first battery 51 and the second battery 52 and operative to be chargeable each other between the first battery 51 and the second battery 52 by converting each other's output between the first battery 51 and the second battery 52, for example, even if the emergency situation, in which the wheel platform 15 cannot be moved because of no electric power of the second battery 52, takes place, the wheel platform 15 can be moved by utilizing the remained electric power in the first battery 51.

It will be understood by those of skill in the related arts that the descriptions herein necessarily incorporate the features, devices, structures, circuits, pathways, linkages, and other physical and electronic structures and constructions to accomplish the purposes herein. For example, first battery 51 will be understood to be capable of accomplishing the purpose of a battery—charge storage, intake, discharge, connection to related systems, etc. as would be understood within the scope of the electrical battery art following study of the discussion herein. Similarly, any circuit, such as a conversion circuit or other electronic circuit will be understood to contain the electronic pathways and components, and other elements to accomplish the purposes herein, as would be understood within the scope of the battery art following study of the discussion herein.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

EXPLANATION OF REFERENCES

3 X-ray tube
12 Collimator
13 Arm
14 Supporting pole
15 Wheel platform
16 Rear wheel
17 Front wheel
18 Operation handle
31 Glass bulb
32 Cathode
33 Rotary anode
34 Motor rotor
35 Motor stator
37 Radiation window
39 Regenerative brake circuit
40 Control module
41 Sensor
42 Encoder
43 driving motor
44 Regenerative brake circuit
51 First battery
52 Second battery
53 Charge circuit
54 Charge circuit
55 Conversion circuit
56 Charge circuit
61 Console module
62 Commercial power supply

What is claimed is:

1. A mobile X-ray radiographic device, comprising;
a wheel platform including a pair of driving wheels;
a supporting pole extending upwardly on the wheel platform;
an operative X-ray tube on said supporting pole and the supporting pole is operative to elevate said X-ray tube relative to the wheel platform during a use thereof;
a driving motor installed on said wheel platform operative to provide a revolution drive of the driving wheels;
the mobile X-ray radiographic device, further comprising:
a first battery operatively joined to said X-ray tube;
said first battery operative to provide a necessary electric power to generate X-rays from the X-ray tube within a short period of time for said X-ray tube;
the short period of time being less than three seconds;
a second battery operatively connected to the driving motor;

said second battery being constructed to have a lower deteriorative rate than said first battery despite a repeating use cycle of charge and discharge of said second battery;

a regenerative brake circuit operatively connected to said driving motor and operative to output an regenerative electric power from a motion of said driving motor; and a charge circuit operative to charge said second battery by utilizing the regenerative electric power obtained from said regenerative brake circuit.

2. The mobile X-ray radiographic device, according to claim 1, further comprising:

a regenerative brake circuit connected to a rotor motor and operative to rotate an anode relative to said X-ray tube during a use thereof.

3. The mobile X-ray radiographic device, according to claim 2, further comprising:

a conversion circuit operative to convert a charge between said first battery and the second battery by converting an output of one of said first and said second battery to said other of said first and said second battery.

4. The mobile X-ray radiographic device, according to claim 3, wherein:

said first battery is a lead battery; and
said second battery is a lithium battery.

5. The mobile X-ray radiographic device, according to claim 2, wherein:

said first battery is a lead battery.

6. The mobile X-ray radiographic device, according to claim 2, wherein:

said second battery is a lithium battery.

7. The mobile X-ray radiographic device, according to claim 1, further comprising:

a conversion circuit operative to convert a charge between said first battery and the second battery by converting an output of one of said first and said second battery to said other of said first and said second battery.

8. The mobile X-ray radiographic device, according to claim 7, wherein:

said first battery is a lead battery; and
said second battery is a lithium battery.

9. The mobile X-ray radiographic device, according to claim 1, wherein:

said first battery is a lead battery.

10. The mobile X-ray radiographic device, according to claim 1, wherein:

said second battery is a lithium battery.

11. A mobile X-ray radiographic device, comprising;

a wheel platform including a pair of driving wheels;
a supporting pole extending upwardly on the wheel platform;
an operative X-ray tube on said supporting pole and the supporting pole is operative to elevate said X-ray tube relative to the wheel platform during a use thereof;
a driving motor installed on said wheel platform operative to provide a revolution drive of the driving wheels;
the mobile X-ray radiographic device, further comprising:
a first battery operatively joined to said X-ray tube;
said first battery operative to provide a necessary electric power to generate X-rays from the X-ray tube within a short period of time for said X-ray tube;
the short period of time being less than three seconds;
a second battery operatively connected to the driving motor;
said second battery being constructed to have a lower deteriorative rate than said first battery despite a repeating use cycle of charge and discharge of said second battery;
a regenerative brake circuit operatively connected to said driving motor and operative to output an regenerative electric power from a motion of said driving motor;
said regenerative brake circuit also operatively connected to a rotor motor and operative to rotate an anode relative to said X-ray tube during a use thereof; and
a charge circuit operative to charge said second battery by utilizing the regenerative electric power obtained from said regenerative brake circuit.

12. The mobile X-ray radiographic device, according to claim 11, further comprising:

a conversion circuit operative to convert a charge between said first battery and the second battery by converting an output of one of said first and said second battery to said other of said first and said second battery.

13. The mobile X-ray radiographic device, according to claim 12, wherein:

said first battery is a lead battery; and
said second battery is a lithium battery.

* * * * *